US009857225B2

(12) United States Patent
Pearman et al.

(10) Patent No.: US 9,857,225 B2
(45) Date of Patent: Jan. 2, 2018

(54) DUAL SPECTROSCOPIC SYSTEM AND METHOD FOR GAS SAMPLE ANALYSIS

(71) Applicant: IMACC, LLC, Round Rock, TX (US)

(72) Inventors: William F. Pearman, Cedar Park, TX (US); Scott A. Evans, Ingleside, IL (US); Daniel J. Pearson, Chicago, IL (US)

(73) Assignee: IMACC, LLC, Round Rock, TX (US)

( * ) Notice: Subject to any disclaimer, the term of this patent is extended or adjusted under 35 U.S.C. 154(b) by 260 days.

(21) Appl. No.: 14/663,882

(22) Filed: Mar. 20, 2015

(65) Prior Publication Data
US 2015/0192468 A1 Jul. 9, 2015

Related U.S. Application Data

(60) Provisional application No. 61/955,994, filed on Mar. 20, 2014.

(51) Int. Cl.
*G01J 3/45* (2006.01)
*G01B 9/02* (2006.01)
*G01J 3/453* (2006.01)
*G01N 21/3504* (2014.01)
*H04B 1/403* (2015.01)

(52) U.S. Cl.
CPC .......... *G01J 3/453* (2013.01); *G01N 21/3504* (2013.01); *H04B 1/406* (2013.01); *G01J 2003/4534* (2013.01); *G01N 2201/06113* (2013.01)

(58) Field of Classification Search
CPC ...... G01J 3/44; G01J 3/45; G01J 3/453; G01J 2003/4534; G01J 3/4535; G01N 21/3504
See application file for complete search history.

(56) References Cited

U.S. PATENT DOCUMENTS 5,164,788 A * 11/1992 Yoshikawa ........... G01J 3/4535
356/452
6,937,324 B2 * 8/2005 Kameoka ........... G01N 21/1702
250/339.08

(Continued)

OTHER PUBLICATIONS

"Passive FTIR Phase 1 Testing of Simulated and Controlled Flare Systems Draft Report", Report, URS Corporation, Oct. 5, 2003.

*Primary Examiner* — Michael A Lyons
(74) *Attorney, Agent, or Firm* — Conley Rose PC

(57) ABSTRACT

A system. The system includes a first beam path configured to transmit a first light beam having a first optical wavelength and a second beam path configured to transmit a second light beam having a second optical wavelength distinct from the first optical wavelength. A first beam splitter disposed at an intersection of the first beam path and the second beam path. The first beam splitter is configured to superimpose the first and second light beams to form a third light beam, the third light beam impinging on a first window of a sample cell. The sample cell defines an interior volume and is configured to transfer the third light beam from the first window to a second window along a light path within the interior volume. The light path comprises a plurality of segments. The third light beam undergoes at least one reflection at an end of each segment, wherein the light path passes through a gas sample disposed within the interior volume.

17 Claims, 10 Drawing Sheets

(56) References Cited

U.S. PATENT DOCUMENTS

| | | | |
|---|---|---|---|
| 7,079,252 B1* | 7/2006 | Debreczeny | A61B 5/14532 356/451 |
| 7,616,316 B1* | 11/2009 | Silver | G01N 21/3504 356/409 |
| 9,513,167 B2 | 12/2016 | Hargreaves | |
| 2009/0173884 A1* | 7/2009 | Nagai | G01J 3/45 250/339.08 |
| 2010/0302546 A1* | 12/2010 | Azimi | G01J 3/02 356/437 |
| 2014/0117238 A1* | 5/2014 | McCann | G01N 21/3504 250/338.4 |
| 2014/0152993 A1* | 6/2014 | Hirao | G01J 3/0289 356/451 |
| 2015/0062586 A1* | 3/2015 | Zhu | G01J 3/45 356/453 |
| 2016/0003676 A1* | 1/2016 | Fukuda | G01J 3/0264 250/339.08 |

* cited by examiner

DUAL SPECTROSCOPIC SYSTEM AND METHOD FOR GAS SAMPLE ANALYSIS

CROSS-REFERENCE TO RELATED APPLICATIONS

This application claims the benefit of U.S. Provisional Application Ser. No. 61/955,994 filed Mar. 20, 2014 and titled "Qualification and Quantification of Flare Vent Gases Using Raman Spectroscopy with a Multi-Pass Optical Cell". The provisional application is incorporated by reference herein as if reproduced in full below.

BACKGROUND

Certain industries, such as the chemical and petroleum industries generate waste gases that need to be controlled. One means of disposing of such waste gases is to burn them in a technique commonly referred to as flaring. Measurement of the constituent gases present in flare vent gas is of importance in assessing the operation of a flare with respect to conformance with environmental regulations. However, there is no single practical method of measuring the components of a gas mixture that can identify all of the potential constituents of flare vent gas of interest in near real time. For example, homonuclear diatomic gas species, such as hydrogen, nitrogen and chlorine, cannot be detected using spectroscopic methods that rely on transitions between states in molecules having a permanent electrical dipole moment. Moreover, commonly used methods that do not rely on molecular dipole transitions such as gas chromatography, are not suited to rapidly changing gas compositions. Therefore systems and methods that address the measurement of flare vent constituent gases are of interest.

BRIEF DESCRIPTION OF THE DRAWINGS

For a detailed description of exemplary embodiments, reference will now be made to the accompanying drawings in which.

NOTATION AND NOMENCLATURE

Figure 1:
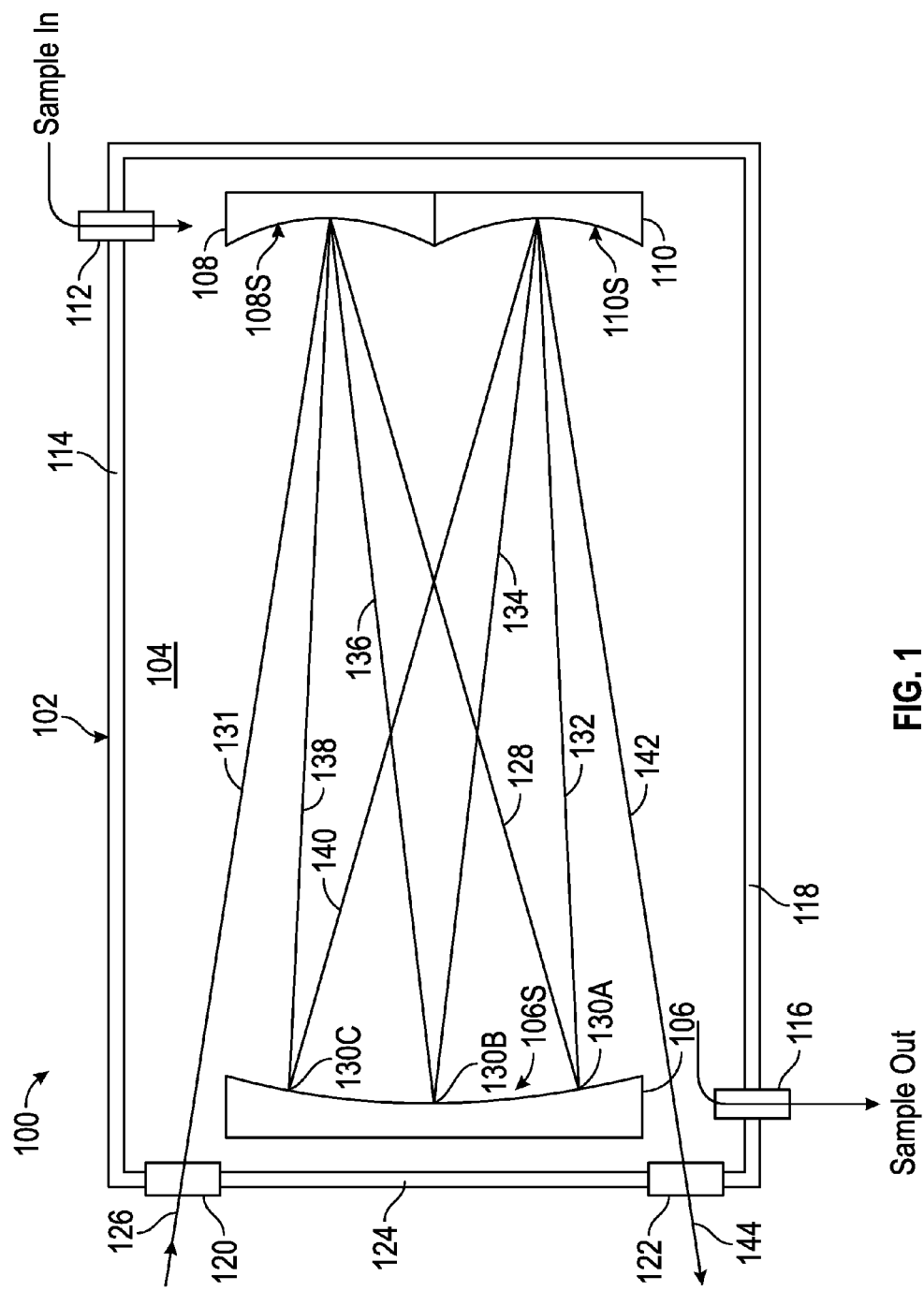
FIG. 1 shows a sample cell in accordance with at least some embodiments.

Certain terms are used throughout the following description and claims to refer to particular system components. As one skilled in the art will appreciate, different companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . . " Also, the term "couple" or "couples" is intended to mean either an indirect or direct connection. Thus, if a first device couples to a second device, that connection may be through a direct connection or through an indirect connection via other devices and connections.

"Light beam" shall mean a directional projection of electromagnetic radiation from a source and having a wavelength range from 300 micrometers (μm or microns) to 100 nanometers (nm).

"About" as used herein in conjunction with a numerical value shall mean the recited numerical value as may be determined accounting for generally accepted variation in measurement, manufacture and the like in the relevant industry.

"Torr" shall mean a unit of pressure equal to 1/760 of an atmosphere.

DETAILED DESCRIPTION

The following discussion is directed to various embodiments of the invention. Although one or more of these embodiments may be preferred, the embodiments disclosed should not be interpreted, or otherwise used, as limiting the scope of the disclosure or the claims. In addition, one skilled in the art will understand that the following description has broad application, and the discussion of any embodiment is meant only to be exemplary of that embodiment, and not intended to intimate that the scope of the disclosure or the claims, is limited to that embodiment.

The foregoing limitations of in the measurement of constituent gases in a gas mixture may be addressed by the application of other spectroscopic techniques. One such is Raman spectroscopy, which is based on the inelastic scattering (referred to as Raman scattering) of photons by molecules in which the polarizability of the molecule changes between states, and does not rely on the molecule of interest having a permanent dipole moment. Raman scattering may use a monochromatic beam of light, which may be a laser beam, in the visible region of the electromagnetic spectrum. The light scattered by the constituent molecules of the gas mixture of interest may be measured, for example, by collecting the light scattered at an angle to the incident light beam. Scattering angles of about 90° or about 180° may typically be used, and may be convenient for remote sensing applications, but other angles may be used, and the described embodiments are not limited to scattering angles of 90° or 180°. Because Raman scattering is inelastic, the observed scattered light is shifted in frequency from the incident light. Thus, as will be described further below, if the frequency of the incident light is denoted $\omega_0$, the Raman-scattered light may have a frequency $\omega_0 \pm \omega_m$ where $\omega_m$ is characteristic of the molecule scattering the incident light. By measuring the frequency, or equivalently the wavelength, of the scattered light, $\omega_m$ may be ascertained and thus the scattering molecule may thereby also be ascertained. By measuring the spectrum of the $\omega_m$, the various constituent gases that otherwise do not have a permanent dipole moment may be determined.

The sensitivity of a Raman scattering-based measurement is directly proportional to the amount of Raman-scattered light produced and then collected in the measuring device.

The Raman-scattered signal (in number of photoelectrons), denoted by S, may be given by equation 1:

$$S=(P_D K)(\beta D)(A_D \Omega_D T Q)t \quad (1)$$

where $P_D$ is the photon flux density of the incident light (photons/unit area/second), K is the path length of the light beam through a sample volume, $\beta$ is the differential Raman scattering cross-section, D is the number density of molecules in the sample, $A_D$ is the area of the sample monitored by the device, $\Omega_D$ is the collection solid angle of the device, T is the transmission of the device and associated optics, Q is a quantum efficiency a detector of the Raman photons and t is an observation time. Turning now to FIG. 1, there is illustrated therein a sample cell 100 in accordance with at least some embodiments, which may be used to increase the Raman signal, S by increasing the path length L, through a sample.

Sample cell 100 includes an enclosure 102 defining an internal volume 104. Disposed within internal volume 104 may be mirror 106, mirror 108 and mirror 110. Each of mirrors 106, 108, 110 may comprise a respective spherical surface portion 106S, 108S, 110S having a reflective material deposited thereon. Example reflective materials may include silver, aluminum and gold. Further, a coating may be deposited on the reflective material. Such a coating may be used to provide corrosion resistance to the mirrors, particularly in applications in which the sample gases include chemically reactive constituents. Magnesium fluoride is an example coating material which used, but any other suitable coating material may be used.

A sample gas mixture to be analyzed may be introduced into interior volume 104 via sample inlet and outlet ports. A sample to be analyzed may be introduced into interior volume 104 through a sample inlet port 112. Sample inlet port 112 may be disposed within, and provide a passageway through a wall 114 of enclosure 102. Sample inlet port 112 may be connected to a tube or similar structure (not shown in FIG. 1) introduced into or connected to a gas source to be analyzed. Similarly, sample outlet port 116 may vent or exhaust the sample from interior volume 104. Sample outlet port 116 may be disposed within, and provide a passageway through, a wall 118 of enclosure 102. Sample outlet port 116 may be connected via tubing or the like to an exhaust plenum or other structure (neither shown in FIG. 1) to effect the safe disposal of the sample.

Ingress into and egress out of interior volume 104 of a light beam may be effected via windows 120 and 122. Windows 120 and 122 may be disposed within and through a wall 124 of enclosure 102. A light beam 126 may, for example, be transmitted through a window 120 from a source such as a laser, and into interior volume 104. Light beam 126 may comprise wavelengths in the visible portion of the electromagnetic spectrum, the ultraviolet portion of the spectrum, or in the infrared portion of the electromagnetic spectrum, or, in at least some embodiments, combinations thereof, as described further below. In an embodiment having a light beam 126 comprising wavelengths in disparate portions of the electromagnetic spectrum, light beam 126 may be a superposition of light beams from different sources, also described further below. Nevertheless, for the purpose of the description of the passage of light beam 126 through sample cell 100, it would be understood by those skilled in the art having the benefit of the disclosure, that it is immaterial whether light beam 126 comprises light from one or a plurality of sources.

Light beam 126 entering window 120 may impinge on spherical surface portion 108S of mirror 108 and be reflected toward mirror 106 along a path 128 where it impinges on spherical surface portion 106S at a first point, 130A. The light beam may then be reflected back toward mirror 110 along a path 132 and impinging on spherical surface portion 110S of mirror 110. A reflection by mirror 110 may return the light beam along a path 134 back toward mirror 106 where it may be reflected by mirror 106 at a second point, 130B. Mirror 106 may reflect the light beam again, now along a path 136 toward mirror 108. Mirror 108 may again reflect the light beam back toward mirror 106 along a path 138 where it impinges on spherical surface portion 106S at a third point, 130C. Light reflected by mirror 106 at point 130C may proceed along a path 140 toward mirror 110. Mirror 110 may reflect the light beam again where the light beam may proceed along a path 142 to exit interior volume 104 through window 122 as light beam 144. In traversing through interior volume 104 of sample cell 100, the light beam may interact with the gas sample disposed within interior volume 104. As described further below, depending on the physical process by which the light and constituents of the gas sample interact, light beam 144 that exits sample cell 100 may include electromagnetic radiation having wavelengths that are different from the wavelengths of the incident light comprising light beam 126. Likewise, the total energy, and the energy in any particular wavelength, in light beam 144 may be reduced from the incident optical energy in light beam 126.

Together with path 131, paths 132-140 define an optical path through cell 100 from window 120 to window 122. Each of the paths 131, 132, 134, 136, 138 140 and 142 may be considered one of eight segments of the optical path and having one or both of their respective ends at a reflection point on the set of mirrors 106-110. Stated otherwise, the optical path includes a plurality of segments each having at least one reflection at an end thereof. While example cell 100, has eight segments, other cells may include may have other numbers of segments, or passes, therein. In at least some embodiments, a cell may have from 3 to 15 passes and in still other embodiments, as many as one hundred passes.

Figure 2A:
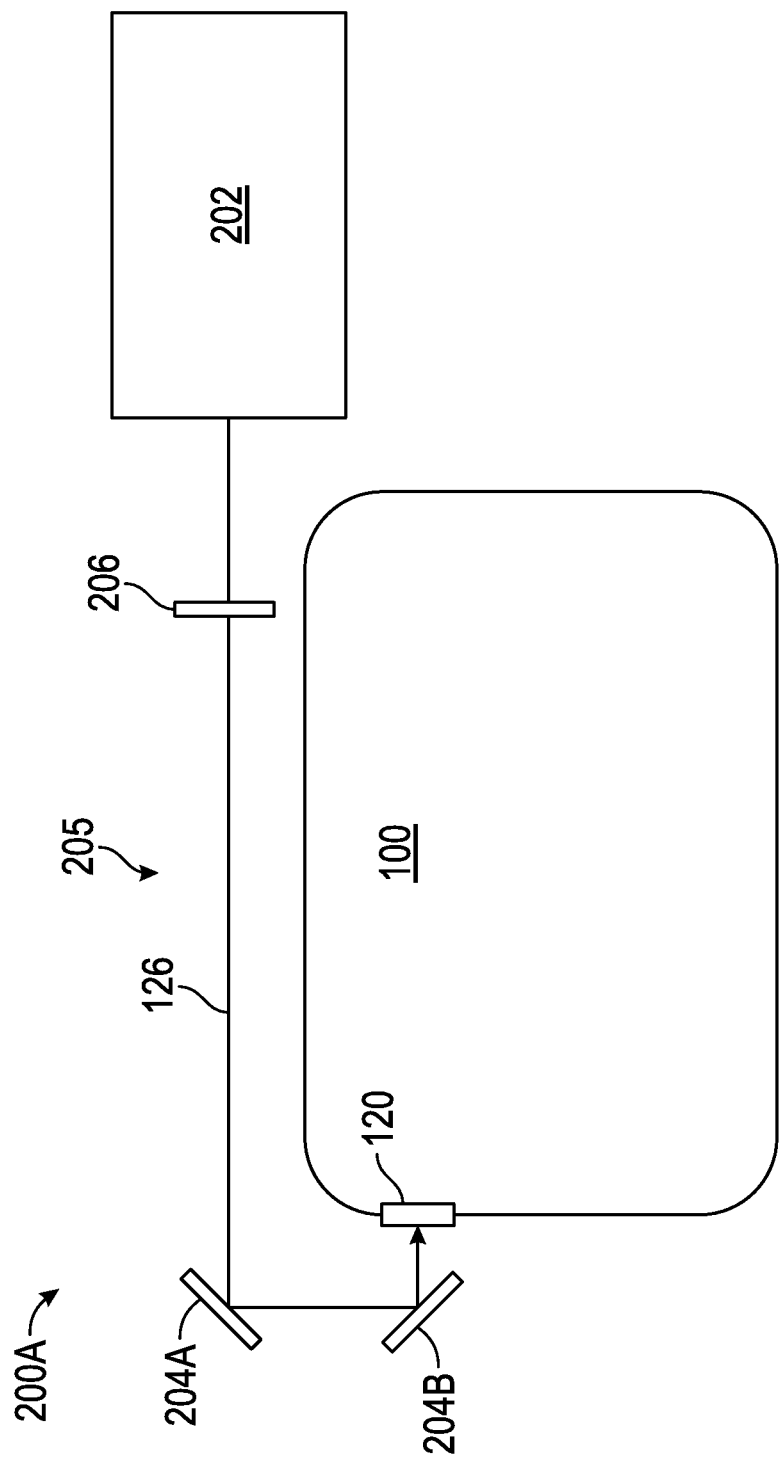
FIG. 2A shows an optical energy delivery system in accordance with at least some embodiments.

As described above, optical energy may be delivered to sample cell 100 in the form of a light beam transmitted through a window in a wall of the sample enclosure. FIG. 2A illustrates an exemplary optical energy delivery system 200A in accordance with at least some embodiments. Light beam 126 may be generated by a source 202 and impinge on one or more turning mirrors 204. For example, turning mirror 204A may reflect light beam 126 onto turning mirror 204B and further reflected by turning mirror 204B. On reflection from turning mirror 204B, light beam 126 may be impinge on window 122 and enter sample cell 100 as previously described. Alternatively, in at least some embodiments, beam path 205 may comprise a fiber optic (not shown in FIG. 2A), and one or both of turning mirrors 204A, 204B may be absent. Source 202 may comprise a laser generating a collimated beam of light. The wavelength of the light may be in the infrared, visible or ultraviolet portions of the electromagnetic spectrum in accordance with the particular physical interaction between the light beam and gas sample of interest. For example, for Raman scattering spectroscopy of a gas sample, wavelengths in the visible portion of the spectrum may be used. In such an exemplary embodiment, source 202 may be a diode-pumped solid state laser have a wavelength in the range from about 500 nanometers (nm) to about 670 nm, and a power in the range of about 50 milliwatts (mW) to about 400 mW. However, the principles of the disclosure are not limited to such a laser source, and other laser systems may be used in conjunction with the systems described herein. A bandpass filter 206 may be disposed in an optical path between source 202 and turning mirror 204A. In an embodiment in which source 202 comprises a laser, bandpass filter 206 may be used to filter out optical energy in light beam 126 lying outside of the primary lasing mode of source 202, which may be the TEM000 mode of the laser. In this way, in an embodiment employing Raman spectroscopy, for example, a multiplicity of scattering peaks in the spectrum of the light beam 144 exiting sample cell 100 arising from mode hopping in source 202 may be avoided.

Figure 2B:
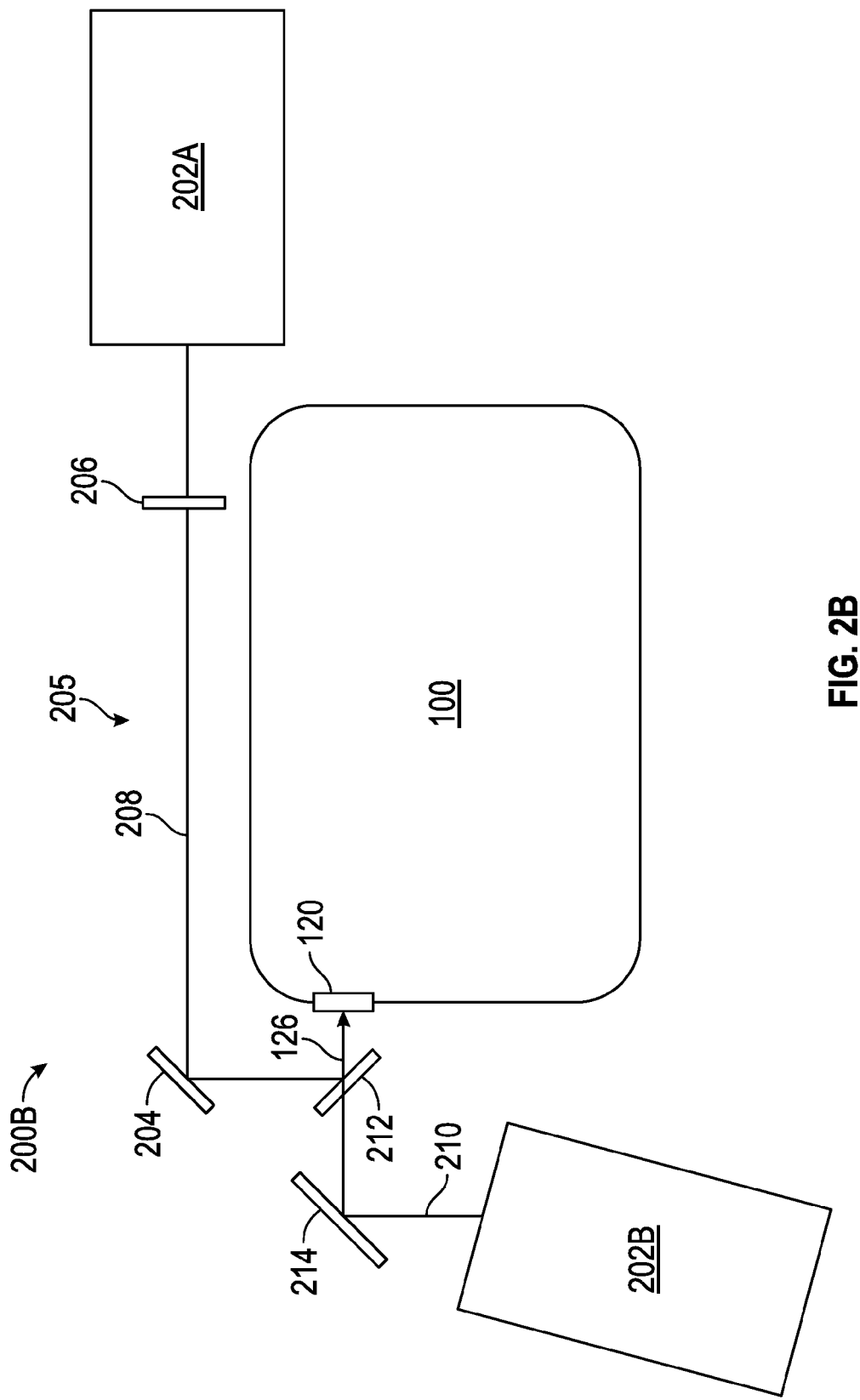
FIG. 2B shows another optical energy delivery system in accordance with at least some embodiments.

As described previously, the different molecular species within a sample may be amenable to detection by different physical processes in the interaction with a light beam. In at least some embodiments, a sample cell 100 may be used in conjunction with a combination of such physical processes. Thus, in such embodiments, light beam 126 may, for example, be a composite, or superposition of light beams having different wavelengths as may be appropriate for the different light-molecule interactions used to detect and quantify the various constituent species in a sample. FIG. 2B shows an optical energy delivery system 200B that may be used in conjunction with a sample cell 100 and a light beam 126 comprising a composite, or superposition, of light beams from separate sources 202A, 202B and which may have different wavelengths, and/or other properties as appropriate to the detection of different constituent species in the sample. For example, source 202A may generate a light beam 208 in a visible portion of the electromagnetic spectrum which may be used in conjunction with Raman spectroscopy to detect constituent species without an electric dipole moment, and source 202B may generate a light beam 210 in the infrared portion of the electromagnetic spectrum which may be used to detect constituent species having an electric dipole moment. Light beams 208 and 210 may be superposed via dichroic beam splitter 212 to form a composite light beam, light beam 126, as described hereinabove. In the example optical energy delivery system 200B, turning mirrors 204 and 214 may be included to steer light beams 208 and 210, respectively onto dichroic beam splitter 212. However, as a person skilled in the art having the benefit of the disclosure would appreciate, in other embodiments one or both turning mirrors 204, 214 may be absent in some embodiments of a system employing an optical energy delivery system such as system 200A. In at least some embodiments, source 202B may comprise a source of optical energy and/or additional optical elements based on the spectroscopic techniques used to detect the various constituent species of the sample. For example, source 202B may comprise a Fourier transform infrared spectroscopy (FTIR) source, as described further below.

Figure 3A:
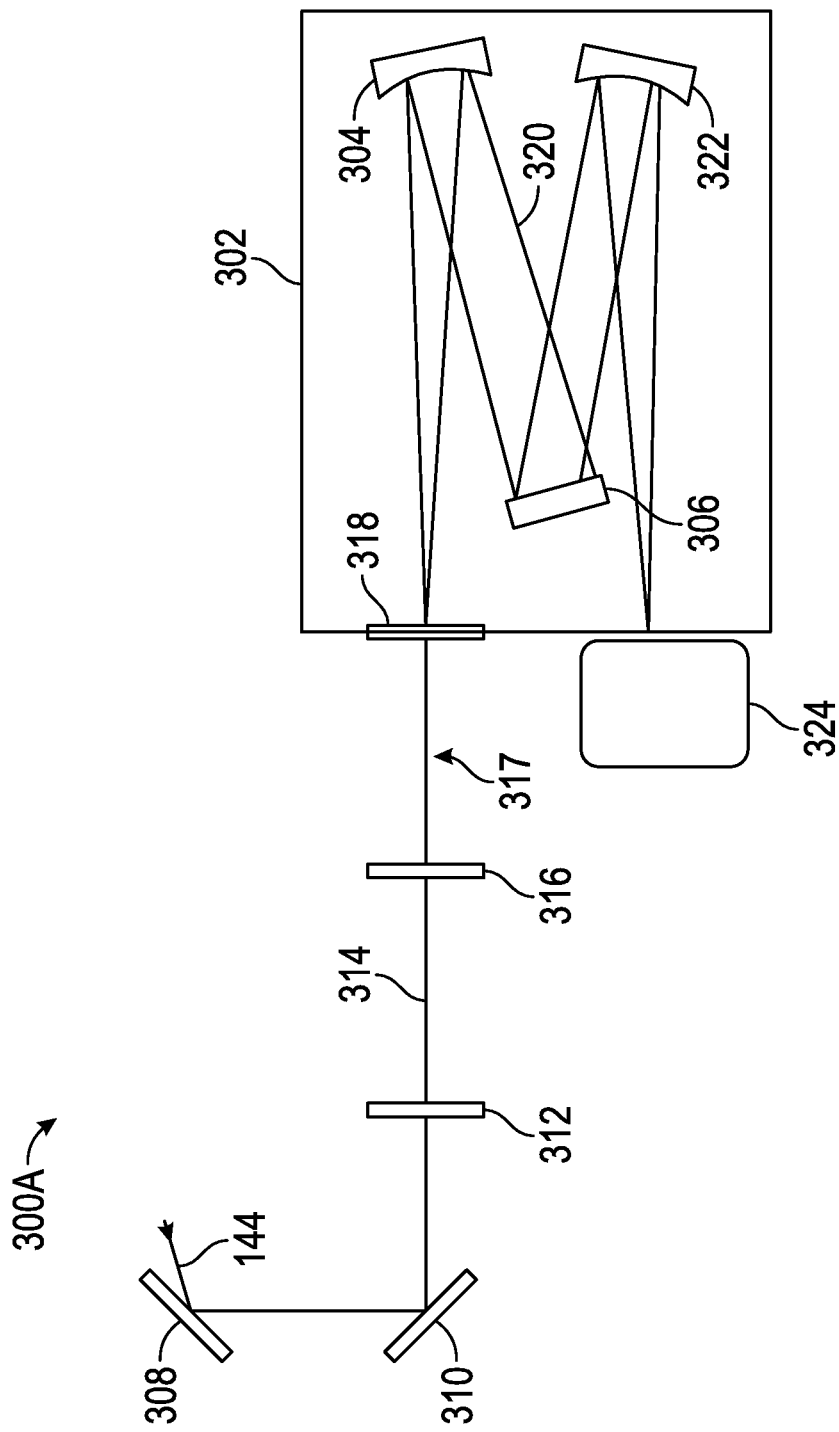
FIG. 3A shows optical path in accordance with at least some embodiments.

Turning now to FIG. 3A, there is shown an exemplary optical path 300A for a light beam 144 between sample cell 100 and a spectrometer 302 in accordance with at least some embodiments. Spectrometer 302 may include a collimating mirror 304 and a dispersing element 306. In the exemplary optical path 300A, light beam 144 may imping on a turning mirror 308 and reflected thereby onto a turning mirror 310. In at least some other embodiments one or both turning mirrors 308, 310 may be absent based on the particular configuration of a system employing an optical path such as optical path 300. As previously described, light beam 144 may include optical wavelengths different from the optical wavelengths comprising the incident light beam 126. For example, interaction of the incident light beam and constituent species in the sample by a Raman scattering process generates electromagnetic radiation shifted in frequency, and thus in wavelength, from the frequency of the incident light beam by a frequency characteristic of the scattering species. Thus, optical path 300A may include a rejection filter 312 to remove the optical energy at the wavelength of the incident light beam 126 from light beam 144. Light beam 314 may then comprise wavelengths that are shifted in wavelength from the wavelength of the incident light beam based on the constituent species in the sample. Light beam 314 may be focused by focusing optics 316 onto entrance slit 318 of spectrometer 302. In at least some embodiments, a segment 317 of optical path 300A may include an optical fiber coupling focusing optics 316 and entrance slit 318, and focusing optics 316 may focus light beam 314 into the optical fiber. Entrance slit 318 may be in the object space of collimating mirror 304 and positioned at a focal plane thereof. Light beam 320, collimated by collimating mirror 304, impinges on dispersing element 306 which may resolve light beam 320 into is spectral components. The spectrally resolved light beam may then be focused by focusing mirror 322 thereby forming a spectrally resolved image of entrance slit 318 on detector 324. Detector 324 may include photoelectric elements, for example, converting the spectrally resolved optical energy impinging thereon into electrical signals proportional to the intensity of the light in each of the component wavelengths in light beam 320. In at least some embodiments, detector 324, or portions thereof, may be cooled by a thermoelectric cooler, or, in other embodiments, by a cryogenic fluid such as liquid nitrogen. The electrical signals may be digitized for subsequent automated analysis, as described further below. A system employing a optical path substantially in the form of optical path 300A will be described in conjunction with FIG. 4A.

Figure 3B:
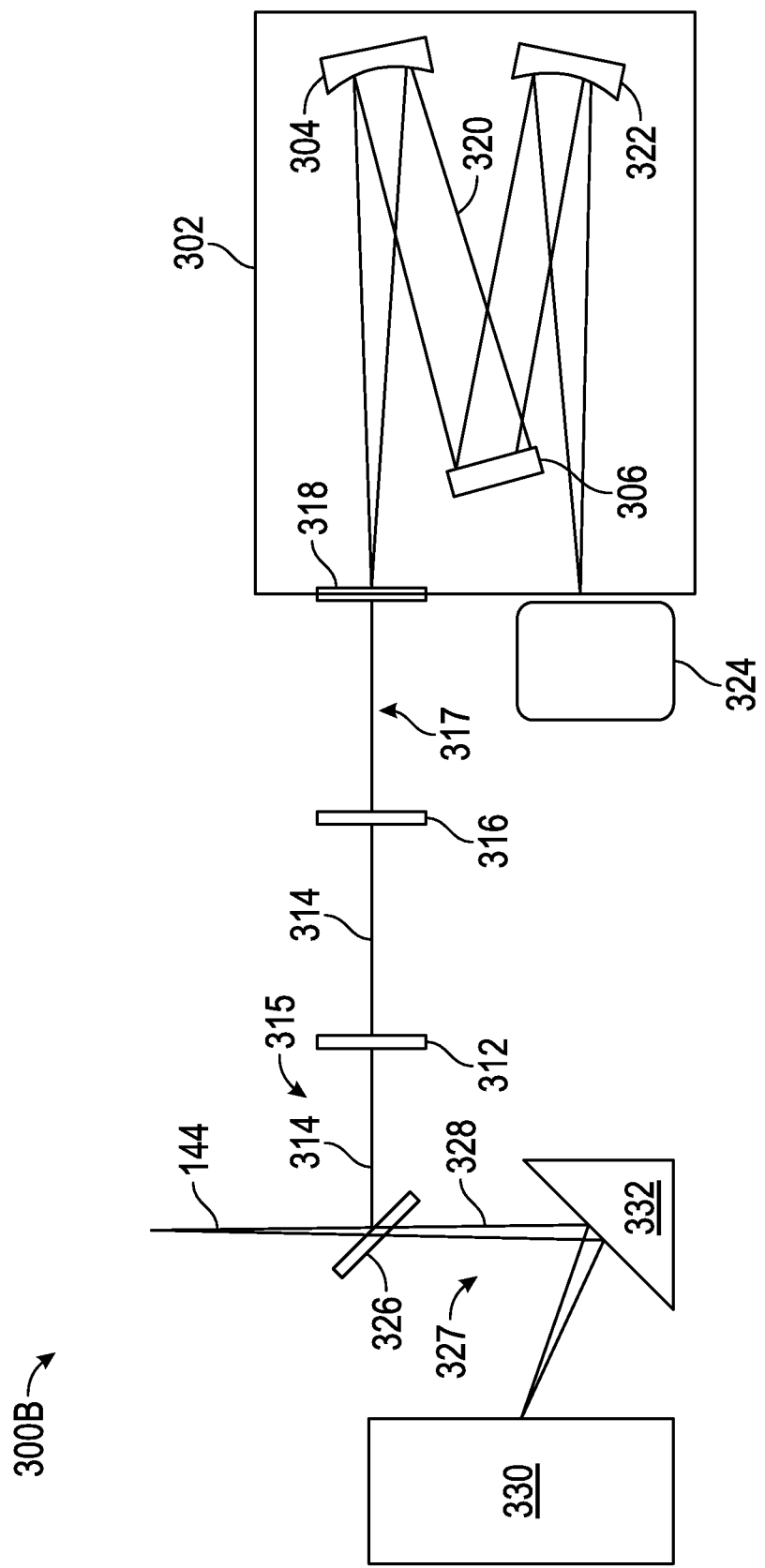
FIG. 3B shows another optical path in accordance with at least some embodiments.

Turning now to FIG. 3B, there is shown another exemplary optical path 300B in accordance with some embodiments. Similar to optical path 300A, light beam 144 may comprise a multiplicity of optical wavelengths in addition to the wavelengths of the light beams incident on sample cell 100. Light beam divide light beam 144 along two optical paths, 315 and 327 and split light beam 144 into a portion comprising light beam 314 as described above, and another portion, light beam 328. Light beam 328 may comprise the remaining optical energy in light beam 144 and have optical wavelengths distinct from the optical wavelengths of the optical energy in light beam 314. For example, the optical wavelengths of portion 328 may be in the infrared portion of the electromagnetic spectrum corresponding to optical source 202B and light beam 314 have optical wavelengths in the visible region of the electromagnetic spectrum. As described above, light beam 314 is optically coupled to spectrometer 302, via optical path 315 in optical path 300B. Light beam 328 may be directed along optical path 327 and focused onto a detector 330 by a focusing element 332. Focusing element 332 may be, in at least some embodiments, an elliptical mirror. However, any suitable focusing element may be used. Detector 330 may generate an electrical signal based on an intensity of light beam 328. A system employing a optical path substantially in the form of optical path 300B will be described in conjunction with FIG. 4B.

Figure 4A:
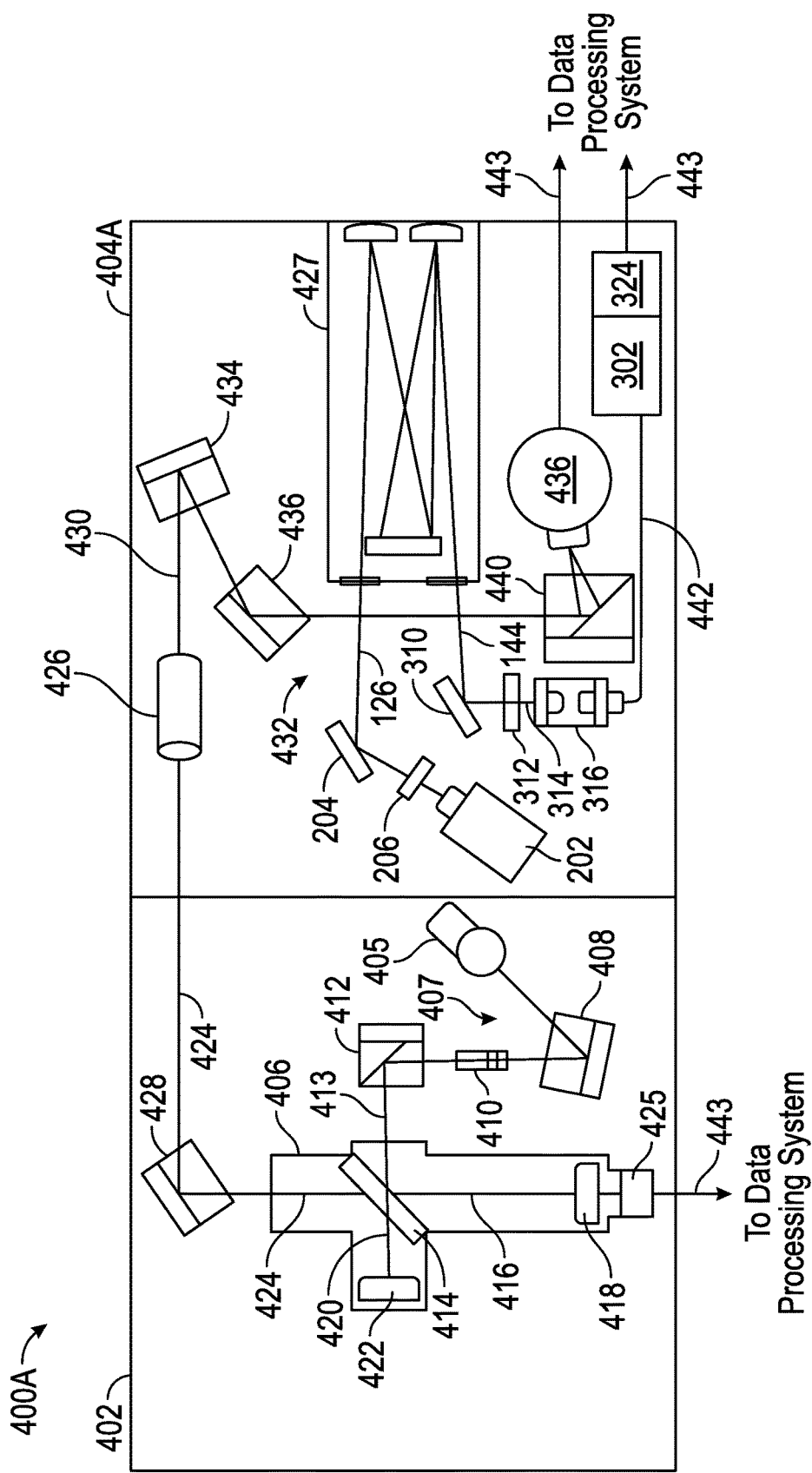
FIG. 4A shows a schematic diagram of a system in accordance with at least some embodiments.
Figure 4B:
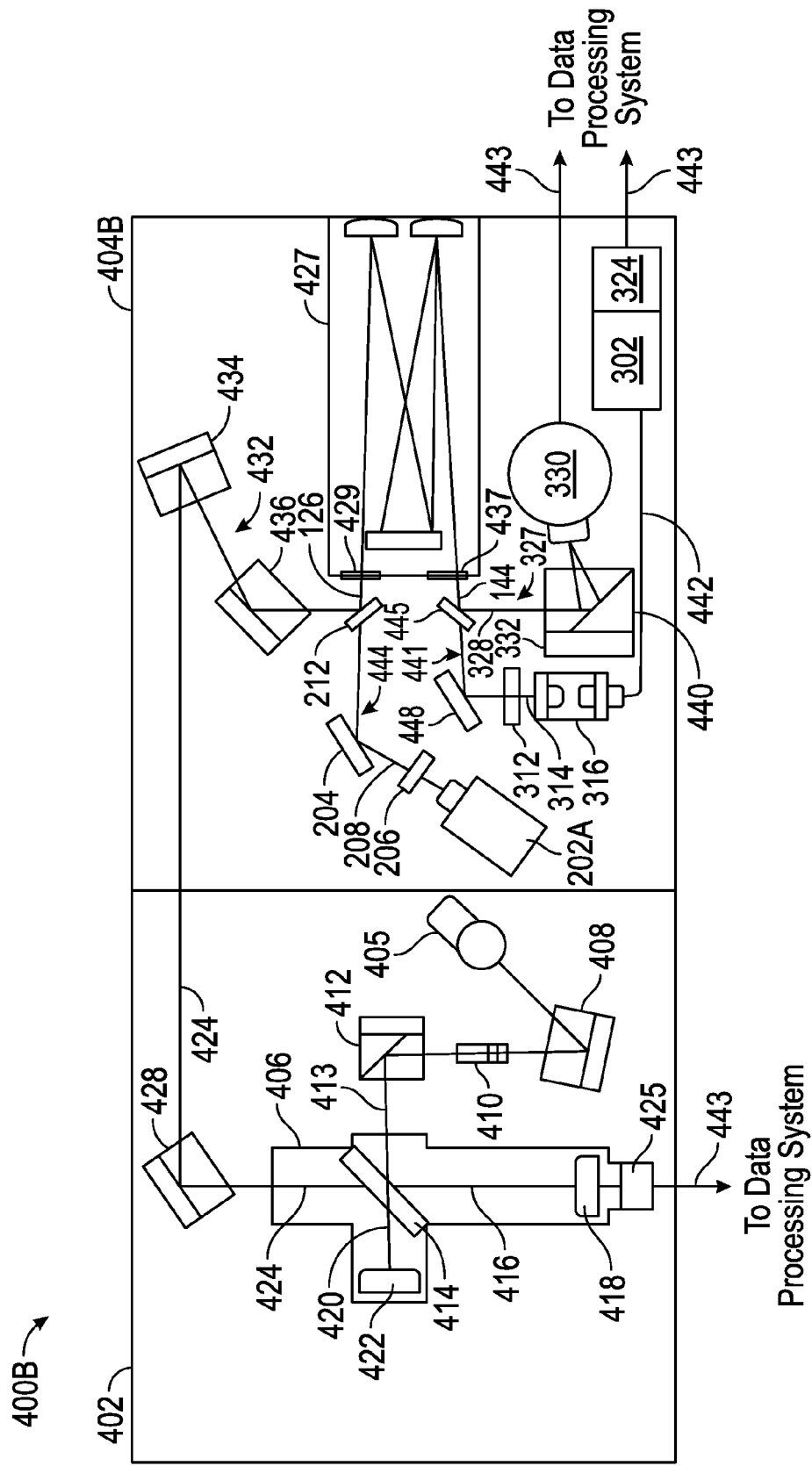
FIG. 4B shows a schematic diagram of another system in accordance with at least some embodiments.

Consider now FIGS. 4A and 4B showing, respectively, exemplary systems 400A and 400B which may be used to analyze the constituents in a gas sample in accordance with at least some embodiments of the principles described herein.

Turning first to FIG. 4A, system 400A includes source section 402 which may comprise a Fourier transform infrared (FTIR) source. Source 402 may include an infrared source 405 generating radiation in the infrared portion of the electromagnetic spectrum and an interferometer 406. Infrared source may 405 may be a black-body source such as a tungsten lamp or similar electrically heated resistive element. An optical path 407 between infrared source 405 and interferometer 406 may be defined by turning mirror 408, aperture 410 and off-axis-parabola 412. Aperture 410 may be included to establish a resolution of an FTIR spectrum. Obtaining an FTIR spectrum in accordance with the disclosed embodiments will be described further below. Off-axis parabola 412 may be incorporated to collimate the light from infrared source 405 and reflect the light beam 413, collimated by off-axis parabola 412, onto beam splitter 414 in interferometer 406. A portion of light beam 413, light beam 416, is reflected by beam splitter 414 onto mirror 418 in interferometer 406 and another portion, light beam 420, is transmitted through beam splitter 414 and impinges on mirror 422 in interferometer 406. Each of light beams 416, 420 is reflected back on itself by a respective one of mirrors 418, 422 and coherently superposed at beam splitter 414, forming light beam 424. An intensity of light beam 424 may comprise an interferogram generated by the constructive/destructive interference of electromagnetic fields comprising light beams 416, 420 based on the relative phase of the electromagnetic fields at each wavelength of a spectrum of the light beams. The relative phase may be varied by changing a distance between a reflecting surface of one of the mirrors in interferometer 406 and beam splitter 414. For example, mirror 418 may be adjustable such that the distance between the reflecting surface of mirror 418 and beam splitter 414 may be varied, wherein infrared radiation comprising light beams 416, 420 having a particular wavelength either constructively or destructively interfere at beam splitter 414. As the distance between mirror 418 and beam splitter 414 is varied over a range of values, the interferogram in light beam 424 may be generated. By way of illustration, in the simple case where infrared source 405 were monochromatic, the mutual constructive and destructive interference between light beam 416 and light beam 420 would generate an intensity pattern that varied cosinusoidally as the distance between mirror 418 and beam splitter 414 is varied. The cosinusoidal intensity pattern constitutes an interferogram generated by interferometer 406. In the more general case where infrared light source is not monochromatic, the interferogram cannot be simply described as a cosinusoid as in the monochromatic case, although the intensity of the light beam comprises an interferogram nonetheless. In at least some embodiments, source section 402 may include a drive unit 425 mechanically coupled to mirror 418 to vary the distance between mirror 418 and beam splitter 414. Drive unit 425 may be coupled to a data processing system via network link 443 and be operated under the control of the data processing system as described further below.

System 400A also includes an analytical section 404A. Analytical section 404A includes an absorption cell 426 optically coupled to interferometer 402 via turning mirror 428 which reflects light beam 424 onto absorption cell 426. Absorption cell 426 may be configured to contain a gas sample for analysis. In at least some embodiments, for example, absorption cell 426 may comprise a sealed vessel capable of operating in a gas sample pressure range of about 250 Torr to about 1000 Torr. Further absorption cell 426 may be configured to be heated. Light beam 424 may pass through absorption cell 426 and interact with constituent molecular species comprising the gas sample based on the infrared absorption characteristics of the constituent molecular species and the wavelengths of the infrared radiation included in light beam 424. A totality of the absorption characteristics of the constituent molecular species in the gas sample defines an infrared absorption spectrum for the gas sample. The interaction modifies the intensity pattern comprising the interferogram of light beam 424 based on an amount of each absorbing molecular species and the wavelengths comprising light beam 424 absorbed by each such species. The modified intensity pattern forms a Fourier transform of the absorption spectrum of the gas sample. Light beam 430, as modified, emerges from absorption cell 426 after traversing a light path within absorption cell 426. In at least some embodiments, the length of the light path in absorption cell 426 may be in the range from about 5 centimeters to 150 centimeters. However, other light path lengths may be used as appropriate to the concentration of absorbing constituent species in the gas sample. For example, for low concentrations of absorbing constituent species, long path lengths may be used, and conversely, short path lengths if the concentration of absorbing species is high. Light beam 430 may then traverse an optical path 432 defined by focusing mirror 434 and turning mirror 436 and focused onto a detector 438 by focusing element 440. Although in the example system 400, absorption cell 426 is shown disposed between turning mirror 428 and focusing mirror 434, absorption cell may be, in at least some other embodiments, be placed in optical path 432 between turning mirror 436 and focusing element 440. In at least some embodiments, focusing element 440 may comprise an elliptical mirror. Detector 438 may generate an electrical signal proportional to the intensity of the interferogram in light beam 430. As described further below in conjunction with FIG. 5, the electrical signal may be output by detector 438 in digital form and coupled to a data processing system. The electrical signal, in either analog or digital form, represents the Fourier transform of the absorption spectrum of the gas sample, as described above. Further, in at least some embodiments, the electrical signal include instrumental effects associated with the system. Stated otherwise, the electrical signal may represent a Fourier transform of the absorption spectrum convolved with a transfer function associated with the system 400, for example an optical bandwidth thereof. Recovery of the absorption spectrum, as described further below in conjunction with FIG. 5, may include deconvolving the Fourier transform to recover the absorption spectrum of the gas sample.

Analytical section 404A also may include a second cell configured to receive the gas sample, sample cell 427. In at least some embodiments of analytical section 404A, a sample cell 100 may be used for sample cell 427. Sample cell 427 may be used in conjunction a light source, source 202, to analyze molecular species that do not absorb infrared radiation, as previously described. Source 202 may be a laser emitting light in the visible portion of the electromagnetic spectrum as described above in conjunction with FIGS. 2A and 2B. Light emitted by source 202 may be delivered to sample cell 427 via a bandpass filter 206 and turning mirror 204. Light beam 144 exiting sample cell 100 may be directed by turning mirror 310 through rejection filter 312 and filtered light, light beam 314, then impinges on focusing optics 316, as described above in conjunction with FIGS. 3A and 3B. Focusing optics 316 may focus light beam 314 onto fiber optic 442 and coupled thereby to spectrometer 302. The spectrally resolved light from spectrometer 302 may then be converted to electrical signals representative of the spectral components in light beam 314 by detector 324. In at least some embodiments, the electrical signals may be in digital form representing a digitized spectral value based on the number of detected photoelectrons at a wavelength of the spectrum generated by spectrophotometer 302, which also may be electrically coupled to the data processing system, for example, via network links 443.

Turning now to FIG. 4B, system 400B includes source section 402 as in system 400A. Light beam 424 is reflected by turning mirror 428 onto focusing mirror 434. Focusing mirror 434 may comprise a spherical mirror. Similar to system 400A, light beam 424 may traverse an optical path 432 defined by focusing mirror 434 and turning mirror 436 and impinge on dichroic beam splitter 212. A second light beam, light beam 208, generated by source 202A may also impinge on dichroic beam splitter 212 via optical path 444 defined by bandpass filter 206 and turning mirror 204. Source 202A may generate a light beam 208 in a visible portion of the electromagnetic spectrum as described above in conjunction with FIG. 2B. Light beams 424 and 208 may be superposed by dichroic beam splitter 212 to form light beam 126 which is transmitted into sample cell 427 via window 429, similar to window 120 described above in conjunction with FIG. 1. Light beam 144 exiting sample cell 427 via window 437 impinges on dichroic beam splitter 445 which may divide light beam 144 along two optical paths 446 and 327 analogous to dichroic beam splitter 326 and optical paths 315, 327 in FIG. 3B. Similarly, dichroic beam splitter 445 may split light beam 144 into two portions, light beams 314 and 328 comprising different optical wavelengths, as previously described in conjunction with FIG. 3B. Light beam 314 traverses optical path 446 defined by turning mirror 448 and rejection filter 312 to focusing optics 316. Focusing optics 316, fiber optic 442, spectrometer 302 and detector 324 may be configured and operate as described in conjunction with system 400A. Light beam 328 traverses optical path 327 and is focused onto detector 330 by focusing element 332. Detector 330 and focusing element 332 may be configured and operate as described in conjunction with their respective counterparts in system 400A, detector 438 and focusing element 440.

Figure 5:
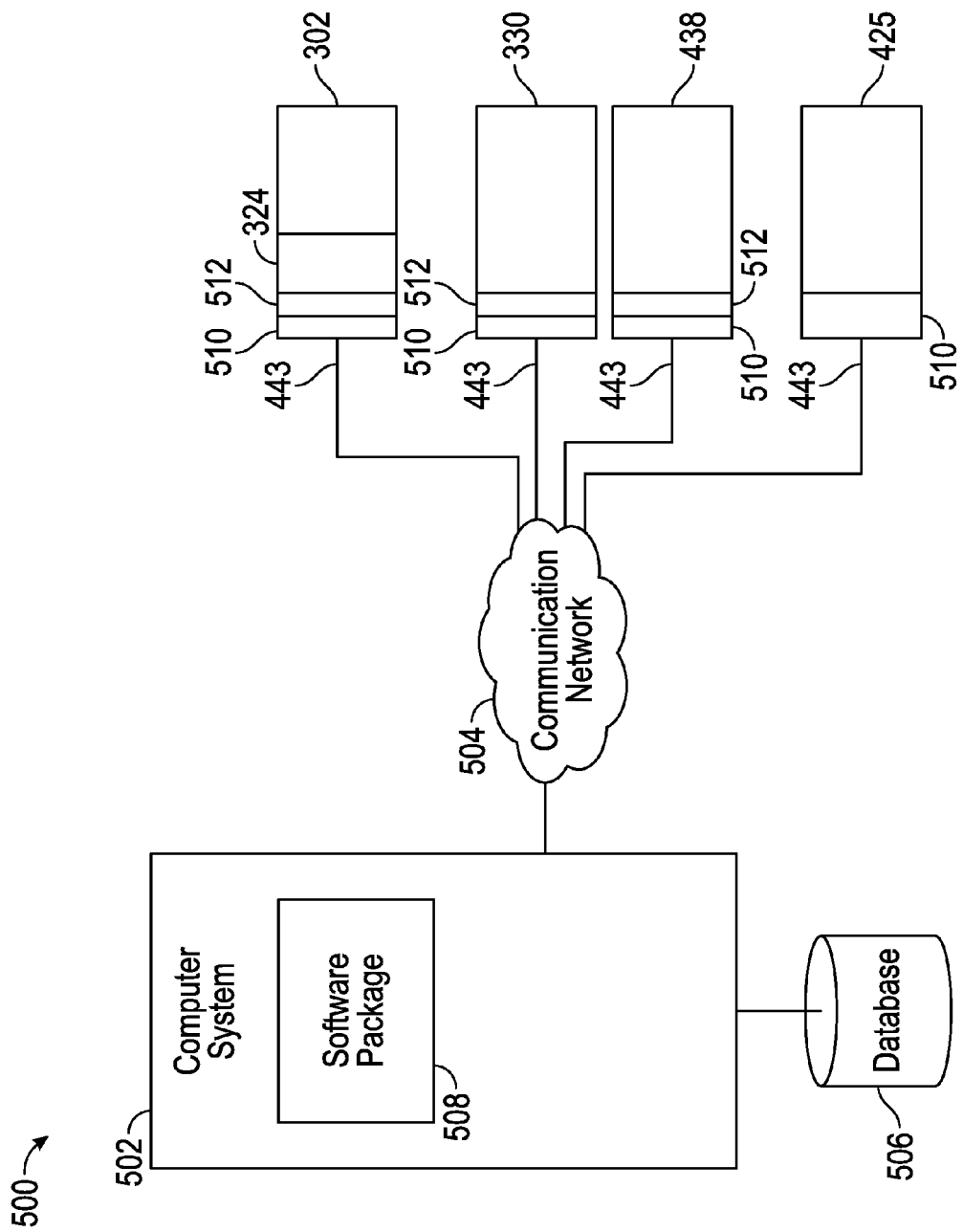
FIG. 5 shows a block diagram of a data processing system in accordance with at least some embodiments.

FIG. 5 shows a block diagram of a data processing system 500 which may be used in conjunction with system 400A or system 400B. Data processing system 500 includes a computer system 502 on which one or more programs may be executed, and a communication network 504 and database 506 connected thereto. Computer system 502 may, in some embodiments, be a server system. In other cases, computer system 502 may be a laptop or desktop computer system. In still other cases, the computer system 502 may be a "cloud" computer system such that the precise location of the computer systems is not known to the user. Regardless of the specific form of computer system 502, it may execute one or more programs, for example software package 508, to control portions of the system (e.g. systems 40A, 400B) for analyzing a gas sample, acquire the data pertaining to a gas sample from the detectors in the systems, analyze the data, and present the results of the analyses as may be prescribed in the programs comprising software package 508. At least some of the data, as described above, may be in the form of spectra characteristic of constituent species in the gas sample. Database 206 may, for example, comprise a library of spectra of constituent species that computer system 502 compares against the acquired data to ascertain the composition of the gas sample.

Each of detectors 324, 330 and 438 and control unit 425 may connect to communication network 504 via a network interface card (NIC) 510. NIC 510 may implement the physical layer (PHY) and media access control (MAC) protocols corresponding to a particular implementation of communication network 504. Communication network 504 may take any suitable form. In some cases, the communication network 208 is a dedicated local- or wide-area network to which the various devices are coupled. In other cases, the communication network may involve in whole or in part the Internet, such as a virtual private network (VPN) carried over the Internet. From a hardware stand point the communication network may involve electrical conductors, optical conductors, radio frequency electromagnetic wave signals propagated point-to-point, and/or satellite based communication. Regardless of the type of communication network used, the computer system 502 communicates with one or more of detectors 324, 330, 438 and drive unit 425 to control the systems and acquire the data therefrom. Further, as previously described, detectors 324, 330 and 438 may include circuitry to convert analog data to digital signals, e.g. digitizers 512, for communication across a network and analysis by computer system 502.

Figure 5A:
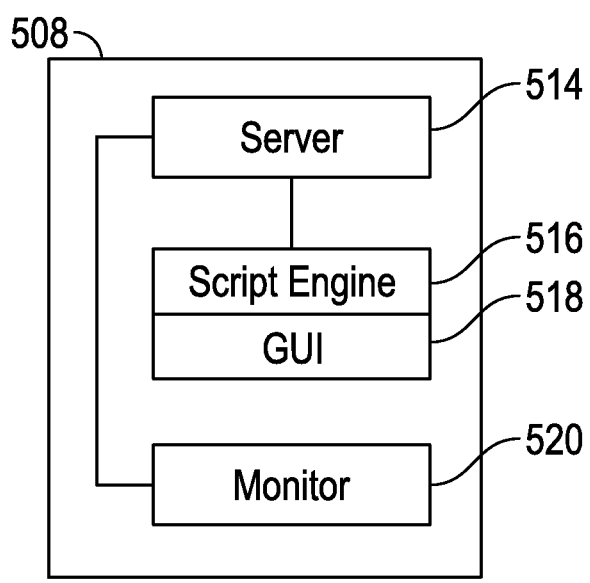
FIG. 5A shows a portion of the data processing system of FIG. 5 in further detail.

Computer system 502 may perform data acquisition and control via one or more programs in software package 508. Referring to FIG. 5A, software package may comprise a server 514, script engine 516 which may be associated with a graphical user interface (GUI) 518, and a monitor 520. Server 514 communicates with the sample analysis system, such as exemplary systems 400A, 400B and performs the analysis of the data acquired therefrom. Server 514 may also control drive unit 425, as previously described, in conjunction with the acquisition of data. Server 514 may then make that data available to other components of the system, such as a user interface, described below. Server 518 may also write the results of the analyses to a nonvolatile storage device, such as a hard drive or solid-state drive in computer system 502 (not shown in FIG. 5) or to database 506. Server 514 controls the data acquisition and operation of the sample analysis systems under the direction of script engine 516. In at least some embodiments, script engine 516 may be based on MICROSOFT Visual Basic. A GUI 518 may be included in conjunction with script engine 516 to allow a user to conveniently generate or modify a script. Monitor 520 is a user interface that displays operational information pertaining to and the results of the analysis of the data from a gas analysis system, and may be user configurable with respect to display style, layout, type of information displayed and the like. Monitor 520 may be a client of server 514.

Figure 6:
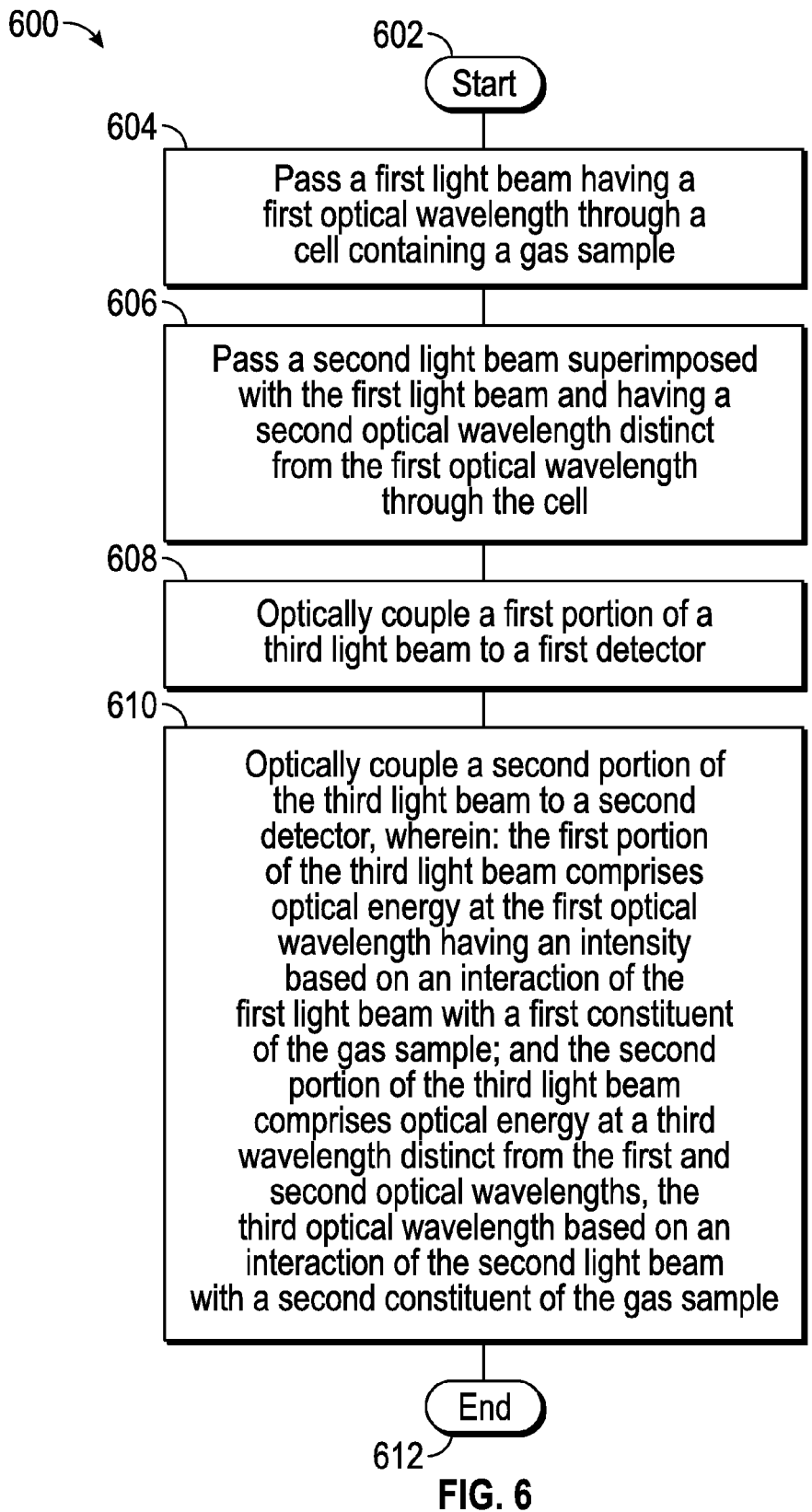
FIG. 6 shows a flow chart of a method in accordance with at least some embodiments.

Referring now to FIG. 6, a method 600 for analyzing a gas sample in accordance with at least some embodiments is shown. Method 600 starts at block 602. In block 604, a first light beam having a first optical wavelength is passed through a cell containing a gas sample. A second light beam superimposed on the first light beam and having a second optical wavelength distinct from the first optical wavelength is passed through the cell, block 606. At block 608, a first portion of a third light beam, is optically coupled to a first detector and at block 610 a second portion of the third light beam, having a third optical wavelength distinct from the first and second optical wavelengths is optically coupled to a second detector. The first portion of the third light beam comprises optical energy at the first wavelength having an intensity based on an interaction of the first light beam with a first constituent of the gas sample. The second portion of the third light beam comprises optical energy at a third optical wavelength distinct from the first and second optical wavelengths. The third optical wavelength is based on an interaction of the second light beam with a second constituent of the gas sample. Thus, for example, if the first optical wavelength is in the infrared region of the spectrum, an interaction with a constituent having a permanent electric dipole moment, as previously described, may be an absorption of some of the optical energy in the first light beam. The second optical wavelength being in the visible portion of the electromagnetic spectrum may give rise to a Raman scattering interaction between the second light beam and another constituent of the gas sample such that the second portion of the third light beam includes optical energy at a Raman-shifted wavelength of the second light beam. Further, the first and second light beams may be superimposed on passing through the cell, and may be passed along an optical path in the cell having multiple reflections between a set of mirrors disposed within the cell. An example optical path may have a length within the cell from about 1 meter (m) to about 10 m. Method 600 ends at block 612.

In the foregoing example, the first detector may generate a first electrical signal based on the intensity of the first portion of the third light beam and the second detector may generate an electrical signal based on a number of photoelectrons generated in response to the second portion of the third light beam. Further the electrical signals from the first and second detectors may be digitized and communicated to a data processing system for analysis. Again considering the example above, the first light beam may comprise an interferogram generated by an interferometer as described in conjunction with FIG. 4A, 4B and the data processing system may compute a Fourier transform of the digitized first electrical signal which comprises a digital representation of an intensity of the interferogram. Further, as previously described, the digitized signal may represent a Fourier transform of the absorption spectrum convolved with instrumentation effects. Thus, in at least some embodiments, the data processing system may deconvolve the Fourier transform to recover the absorption spectrum of constituents of the gas sample having an electric dipole moment. The digitized second electrical signal, comprising a Raman spectrum of other sample constituents, may be compared by the data processing system with a database of Raman spectra characteristic of a set of molecular species.

References to "one embodiment", "an embodiment", "a particular embodiment", and "some embodiments" indicate that a particular element or characteristic is included in at least one embodiment of the invention. Although the phrases "in one embodiment", "an embodiment", "a particular embodiment", and "some embodiments" may appear in various places, these do not necessarily refer to the same embodiment.

The above discussion is meant to be illustrative of the principles and various embodiments of the present invention. Numerous variations and modifications will become apparent to those skilled in the art once the above disclosure is fully appreciated. For example, the layout of the beam paths may be varied as a matter of implementation convenience. These variations are a matter of design choice and do not implicate the principles of the exemplary embodiments described herein. It is intended that the following claims be interpreted to embrace all such variations and modifications.

What is claimed is:

1. A system comprising:
   a first beam path configured to transmit a first light beam having a first optical wavelength,
   a second beam path configured to transmit a second light beam having a second optical wavelength distinct from the first optical wavelength; wherein:
      at least one of the first and second light beams is configured to form a third light beam;
   a first cell defines an interior volume and is configured to transfer the third light beam from a first window to a second window along a light path within the interior volume, the light path comprising a plurality of segments; wherein:
      the third light beam undergoes at least one reflection at an end of each segment; and
      the light path passes through a gas sample disposed within the interior volume;
   a first detector optically coupled to the third light beam and configured to measure an intensity of a first portion of the third light beam;
   a spectrometer optically coupled to a second portion of the third light beam and configured to generate a spectrum of the second portion of the third light beam;
   a second detector optically coupled to the spectrometer, the second detector configured to generate a digitized value based on a number of photoelectrons detected at a wavelength of the spectrum generated by the spectrometer;
   a third detector configured to measure an intensity of an interferogram comprising the second optical wavelength, wherein the third detector comprise a digitizer configured to digitize the intensity of the interferogram; and
   a data processing system communicatively coupled to the third detector wherein the third detector is configured to receive the digitized intensity of the interferogram and generate a Fourier transform of the digitized intensity of the interferogram.

2. The system of claim 1 further comprising:
   a first beam splitter disposed at an intersection of the first beam path and the second beam path, wherein, the first beam splitter is configured to superimpose the first and second light beams to form the third light beam.

3. The system of claim 2 wherein the gas sample comprises a flare vent gas sample.

4. The system of claim 2 further comprising:
   a first light source having the first optical wavelength optically coupled to the first beam path; and
   a second light source having the second optical wavelength optically coupled to the second beam path.

5. The system of claim 4 wherein:
   the first light source comprises a laser generating a light beam in the wavelength range from about 500 nanometers (nm) to about 670 nm; and
   the second light source generates a light beam in the infrared portion of the electromagnetic spectrum.

6. The system of claim 2 wherein the light path within the interior volume has a length in the range of about 1 meter of about 10 meters.

7. The system of claim 2 wherein the first cell is configured to operate at a sample pressure from about 250 Torr to about 1000 Torr.

8. The system of claim 2 wherein:
   the second window is configured to transmit the third light beam external to the interior volume, wherein the third light beam transmitted external to the interior volume comprises the second optical wavelength and a third optical wavelength distinct from the first and second optical wavelengths; and
   the system further comprises a second beam splitter optically coupled to the third light beam, the second beam splitter directing the first portion of the third light beam along a third beam path and directing the second portion of the third light beam along a fourth beam path.

9. The system of claim 8 wherein:

the first portion of the third light beam comprises an optical energy at the first optical wavelength and having an intensity based on an interaction of the second light beam with a first constituent of the gas sample; and the second portion of the third light beam comprises an optical energy at a third optical wavelength based on an interaction of the first light beam with a second constituent of the gas sample.

10. The system of claim 9 wherein:

the first detector is optically coupled to the first portion of the third light beam transmitted external to the first cell; and the spectrometer is optically coupled to the second portion of the third light beam transmitted external to the first cell.

11. The system of claim 10 further comprising an interferometer coupled to the second light source and the second beam path, the interferometer generating the interferogram comprising the second optical wavelength and wherein the intensity of the first portion of the light beam transmitted external to the enclosure comprises an intensity of the interferogram based on the interaction with the first constituent of the gas sample.

12. A system comprising:

the system of claim 1;

a first light source generating the first light beam;

a second light source generating the second light beam;

an interferometer optically coupled to the second light source and configured to generate the interferogram from the second light beam; wherein:

the first cell is optically coupled to the first light beam;

the first cell has an enclosure defining the interior volume, the enclosure comprising:

a first wall having a first port therein, the first port configured to receive the gas sample and pass the gas sample into the interior volume; and a second wall having a second port therein, the second port configured to pass the gas sample out of the interior volume; and a third wall having the first and second windows disposed therein, the first and second windows configured to transmit light impinging thereon, the light path passing through the gas sample and impinging on the second window; and a second cell optically coupled to the interferometer and configured to receive the gas sample, wherein a constituent gas of the gas sample modifies the interferogram based on an absorption spectrum of the constituent gas.

13. The system of claim 12 wherein the first wavelength is in the range from about 500 nanometers (nm) to about 670 nm and the second wavelength is in an infrared portion of the electromagnetic spectrum.

14. The system of claim 12 wherein the third detector is optically coupled to the second cell.

15. The system of claim 12 wherein the data processing system further comprises a database of spectra characteristic of a set of molecular species, the data processing system communicatively coupled to the second detector and configured to compare the digitized value with the database of spectra.

16. The system of claim 12 wherein the second cell is configured to operate in a pressure range of the sample from about 250 Torr to about 1000 Torr.

17. The system of claim 12 wherein the second cell comprises a path length from about 5 centimeters (cm) to about 150 cm.

* * * * *